(12) United States Patent
Yasuda et al.

(10) Patent No.: US 7,871,783 B2
(45) Date of Patent: Jan. 18, 2011

(54) METHOD FOR ACTIVATING AN ANTIGEN, METHOD FOR DETECTING A CELL, AND SOLUTION FOR ACTIVATING AN ANTIGEN

(75) Inventors: Yuichi Yasuda, Kobe (JP); Masakatsu Morita, Kobe (JP); Junyi Ding, Kobe (JP); Rieko Goto, Minoh (JP); Kazuki Kishi, Kobe (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 11/966,318

(22) Filed: Dec. 28, 2007

(65) Prior Publication Data

US 2008/0160542 A1 Jul. 3, 2008

(30) Foreign Application Priority Data

Dec. 28, 2006 (JP) ............................. 2006-355952

(51) Int. Cl.
*G01N 33/53* (2006.01)
(52) U.S. Cl. ........................ 435/7.1; 436/518
(58) Field of Classification Search ...................... None
See application file for complete search history.

(56) References Cited

U.S. PATENT DOCUMENTS

| | | | |
|---|---|---|---|
| 5,424,000 A * | 6/1995 | Winicov et al. ............. | 510/100 |
| 6,592,821 B1 * | 7/2003 | Wada et al. ................. | 422/68.1 |
| 6,960,450 B2 | 11/2005 | Namimatsu | |
| 6,969,585 B2 | 11/2005 | Lorincz et al. | |
| 2002/0182653 A1 | 12/2002 | Namimatsu | |
| 2003/0019049 A9 | 1/2003 | Kravtchenko et al. | |
| 2004/0260157 A1 * | 12/2004 | Montes ........................ | 600/301 |
| 2005/0208529 A1 * | 9/2005 | Winther et al. ................. | 435/6 |
| 2007/0042358 A1 * | 2/2007 | Shah et al. ..................... | 435/5 |

OTHER PUBLICATIONS

Hegmann et al. (J. Cell Biol. 1988 vol. 106, p. 385-392).*
Shi et al. (Biotechnic & Histochemistry 1996 vol. 71, p. 190-196).*
Kimura et al. Acta Histochem Cytochem 1998 vol. 31, p. 453-460.*
Tsukada et al. (Am. J. Pathol. 1987, vol. 126, p. 51-60).*
Smith et al. J. Histochem & Cytochem 1998 vol. 46, p. 731-735.*
Kimura et al. (Acta Histochem. Cytochem. 1998 vol. 31, p. 453-460).*
Kim et al. (J. Molecular Histology 2004 vol. 35, p. 403-408).*
Mohsin et al. (J. Pathology 2003, vol. 199, p. 432-435).*
Pillai et al. (Histopathology 2003 vol. 42, p. 83-87).*
Shi Shan-Rong et al: "Antigen retrieval immunohistochemistry: Past, present, and future"; Journal of Histochemistry and Cytochemistry, vol. 45, No. 34, 1997, p. 327-343 XP-002482118.
Costa P P et al: "Unmasking antigen determinants in amyloid"; The Journal of Histochemistry and Cytochemistry: Official Journal of the Histochemistry Society Dec. 1986, vol. 34, No. 12, Dec. 1986, pp. 1683-1685 XP-002482119.
Robinson J: "Antigen retrieval in cells and tissues"; Acta Histochemica. Cytochem., vol. 35, No. 3, Jul. 16, 2002, p. 203 XP-002482120.
Shujii Yamashita: Progress in Histochemistry and Cytochemistry, vol. 41, Sep. 1, 2006, p. 141-200, pp. 1,2 and 72-73 XP-002482121.

* cited by examiner

*Primary Examiner*—Jacob Cheu
(74) *Attorney, Agent, or Firm*—Sughrue Mion, PLLC

(57) ABSTRACT

A method of activating an antigen is herein described. The method comprises providing an antigen activation solution and contacting the cell with the solution to activate the antigen. A method of detecting a cell fixed by a nonbridging fixation solution is also described. The method comprises providing an antigen activation solution, contacting the cell with the solution, immunostaining the cell, and detecting the stained cell. The solution used for these methods comprises an agent for breaking a hydrogen bond, and is also described herein.

18 Claims, 7 Drawing Sheets

Without antigen activation

With antigen activation

METHOD FOR ACTIVATING AN ANTIGEN, METHOD FOR DETECTING A CELL, AND SOLUTION FOR ACTIVATING AN ANTIGEN

TECHNICAL FIELD

The present invention relates to a method and solution for activating an antigen of a cell fixed by a nonbridging fixation solution.

BACKGROUND

Cytodiagnosis is known as a method for diagnosing diseases by detecting abnormal cells contained in specimens such as sputum, urine, pleural effusion, ascites, bile, aspirates, or sample extracted from uterine cervix. Abnormal cells contained in these specimens are detected on the basis of cell morphology, stained conditions, and other information through the use of, for example, microscopy or flowcytometer after nucleic acid staining or immunostaining.

In cytodiagnosis, cells in a specimen are kept as they are, subjected to staining and other treatments before tests, and then subjected to microscopy or various analyses. Accordingly, it is important to store the cells as they are without being influenced by proteolytic enzymes and others contained in the specimen. Such storage is carried out usually by fixing the cells.

As a method for cell fixation, liquid phase fixation is known, wherein cells are stored in a liquid containing formaldehyde, alcohol, or the like.

For example, as a method of immunostaining fixed cells with a labeled antibody, it is known to activate the antigen of the fixed cells to expose the antigen thereby allowing combination of the antigen with an antibody.

For example, U.S. Pat. No. 6,960,450 discloses a method for activating the antigen of formalin-fixed cells on a glass slide with methylmaleic anhydride.

However, under the conventional method for activation of antigen, a fixed cell must be heated to a temperature of 60 to 121° C. to activate the antigen. In particular, the cells may be damaged by heat applied during the activation of the antigen of the liquid-phase fixed cells, which may hinder precise diagnosis.

BRIEF DESCRIPTION OF THE DRAWINGS

FIG. 4-1 shows the scattergram of cells of proliferative phase obtained from uterine cervix, and FIG. 4-2 shows the scattergram of cells of the secretory phase obtained from uterine cervix.

SUMMARY

Figure 1:
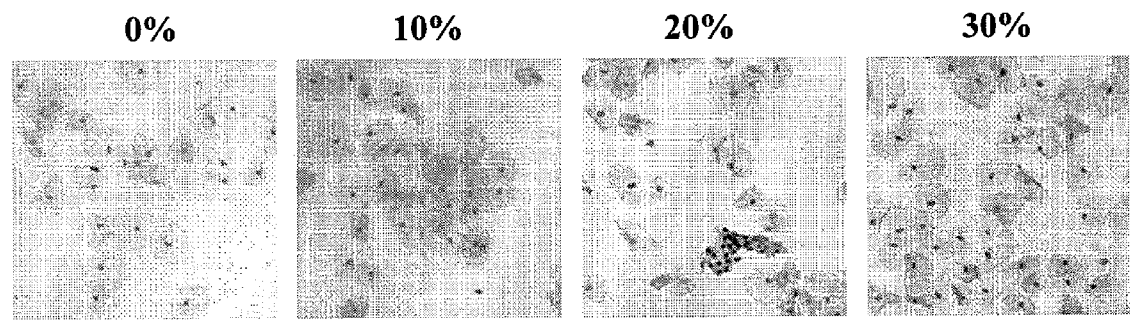
FIG. 1 shows the micrographs of the obtained samples in Experiment 1.

The inventors have attempted to activate the antigen of cells in the liquid-phase fixed sample using a known antigen activation solution, and have found that the antigen was rapidly activated when it reaches a specified temperature. They have also found that the antigen was not activated when the liquid-phase fixed sample was treated with a proteolytic enzyme such as trypsin, pepsin, or papain.

On the basis of these facts, they assumed that hydrogen bonds are present between antigen molecules, between an antigen molecule and nearby molecules, and/or between an antigen molecule and surrounding molecules in the liquid-phase fixed sample, and that cutting of these hydrogen bonds (application of energy exceeding the enthalpy of the hydrogen bonds) exposes the antigen molecules (activates the antigen) thereby allowing antigen-antibody combination.

They also found that the antigen of the liquid-phase fixed cells can be activated with no heat damage to the cells through the use of a liquid containing a substance capable of breaking a hydrogen bond, and have accomplished the present invention.

DESCRIPTION OF THE PREFERRED EMBODIMENTS

The antigen activation solution according to the present embodiment activates the antigen of cells in the sample for liquid based cytology (LBC).

In the present description, "nonbridging fixation solution" refers to a fixation solution containing a nonbridging fixing agent such as alcohol which dehydrates and degreases a cell thereby stabilizing the antigen of the cells with hydrogen bonds. The nonbridging fixation solution stabilizes an antigen mainly with hydrogen bonds, and may contain a bridging fixing agent (a fixing agent such as aldehyde which stabilizes a cell antigen through crosslinking of the protein) to a degree which will not affect antigen activation treatment by the antigen activation solution.

The term "liquid based cytology" refers to a method of diagnosing a disease on the basis of cells suspended in a liquid.

The term "a sample for liquid based cytology" refers to one prepared for the purpose of liquid based cytology, which is obtained, for example, by suspending a specimen extracted from a living body in an appropriate liquid, followed by addition of a fixation solution thereby fixing the cells, or by suspending a specimen extracted from a living body directly in a fixation solution.

In the present description, the method of fixing cells in a liquid as described above is referred to as "liquid phase fixation". For example, fixation through paraffin embedding is not included in the "liquid phase fixation".

Fixation of cells in a sample for liquid based cytology as described above allows transportation of the cells to, for example, an inspection institute with no damage to the cell morphology.

In the present description, the term "antigen activation" refers to exposure of a fixed cell antigen thereby allowing combination of the antigen with an antibody. The antigen activation solution according to the present embodiment activates an antigen on the surface and inside of a cell.

In the present description, the term "fixation" refers to treatment of cells and tissues with minimum change in their morphology and structure for the purpose of preparing diagnostic samples. Typical examples include, but not limited to, formalin fixation and alcohol fixation.

In the present description, the term "specimen" refers to an untreated component which contains cells and is extracted from a living body. Examples are cells extracted from uterine cervix and endometrium, sputum, urine, pleural effusion, ascites, bile, aspirates, and bloods.

The antigen activation solution according to the present embodiment contains an agent for breaking a hydrogen bond. The "agent for breaking a hydrogen bond" is capable of breaking intermolecular hydrogen bonds with preferably minimum influence on cell morphology, and examples thereof include urea, thiourea, polyethylene glycol, glycerol, phenol, acetamide, formamide, sodium thiocyanate, sodium salicylate, lithium bromide, arginine, arginine salts, guanidine, guanidine salts, resorcinol, catechol, dihydroxyacetone, potassium chloride, and magnesium chloride.

The reason that the antigen activation solution is suitable for activating a cell antigen in a liquid phase fixation solution is described below.

When an antigen molecule in a cell or on a cell surface is exposed to the fixation solution which is a far less polar solvent than water, the antigen molecule forms a strong hydrogen bond not with the less polar solvent of the fixation solution but with the more polar molecule in proximity to the antigen molecule. The hydrogen bond changes the structure of the antigen molecule. Resultingly, even if the solvent is replaced with water, the antigen molecule will not readily dissolve in the water. As described above, according to the discussion by the inventors, the reason why the cell antigen stored in the fixation solution is activated by heating the solution is likely due to that the hydrogen bond between the antigen molecule and nearby molecule in the fixation solution is cut by heat energy, and then the antigen molecule attracts water molecules thereby returning to its original structure. If the antigen molecule in the fixation solution is masked only by the surrounding molecules in the solution, the antigen should be activated by treatment with an enzyme which decomposes the molecule. However, the inventors have found that the enzyme treatment cannot activate the antigen.

These facts suggest that the failure in the reaction (or difficulty in the reaction) between the antigen molecule and the antibody in the fixation solution is due to the hydrogen bond between the antigen molecule and nearby molecule (antigen molecule or other molecule) in the fixation solution and/or the hydrogen bond between the molecules surrounding the antigen molecule.

The antigen activation solution according to the present embodiment breaks the hydrogen bond through the action of an agent for breaking a hydrogen bond thereby exposing the antigen, so that the solution activates the antigen without application of heat. The agent for breaking a hydrogen bond is preferably urea because it removes impurities other than a cell contained in the sample, for example, bare nuclei occurring after dissolution of cells, erythrocytes, and mucous threads, thereby facilitating cell detection after the use of the antigen activation solution.

In cytodiagnosis on the basis of cell morphology, it is preferable that morphology of cells to be detected be maintained as much as possible. From that viewpoint, the concentration of the breaking agent in the antigen activation solution is preferably sufficient to activate the cell without significantly affecting the cell morphology, and is appropriately selected according to the type of the breaking agent. For example, when urea is used as the breaking agent, the concentration of the urea in the antigen activation solution is preferably from 10 to 30 w/v %, and more preferably from 10 to 15 w/v %. If the concentration of urea is less than 10 w/v %, the effect in breaking a hydrogen bond may be probably insufficient. In addition, urea denatures protein to damage the cell, so that an antigen activation solution containing urea at a concentration exceeding 30 w/v % probably may damage the cell and nuclei to be detected, and may not be suitable for cytodiagnosis on the basis of morphology. Accordingly, the above-described concentration range is considered preferable. When the concentration is within the range, treatment with the antigen activation solution provides a sufficient effect in breaking a hydrogen bond with minimum deformation of the cells (for example, swelling of nuclei).

The antigen activating agent according to the present embodiment is preferably weakly alkaline. In the present description, the term weakly alkaline refers to a pH range from 7 to 9. When the pH is within the range, activation of antigen is favorably carried out.

In order to keep the pH within the preferable range, the antigen activating agent preferably contains an appropriate buffer. The buffer capable of keeping the pH range from 7 to 9 is preferably the compound expressed by the following general formula (I):

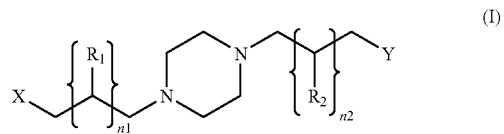

(I)

(wherein X and Y are the same or different from each other, and each represent —OH or —SO$_3$H; R$_1$ and R$_2$ are the same or different from each other, and each represent a hydrogen atom or —OH; and n1 and n2 are the same or different from each other, and each represent 0 or 1). Examples of the compound include 2-[4-(2-hydroxyethyl)-1-piperazinyl]ethanesulfonic acid (HEPES), 3-[4-(2-hydroxyethyl)-1-piperazinyl]propanesulfonic acid (HEPPS), piperazine-1,4-bis(2-hydroxy-3-propanesulfonic acid) dihydrate (POPSO), and piperazine-1,4-bis(2-ethanesulfonic acid) (PIPES). These chemical formulae are shown below.

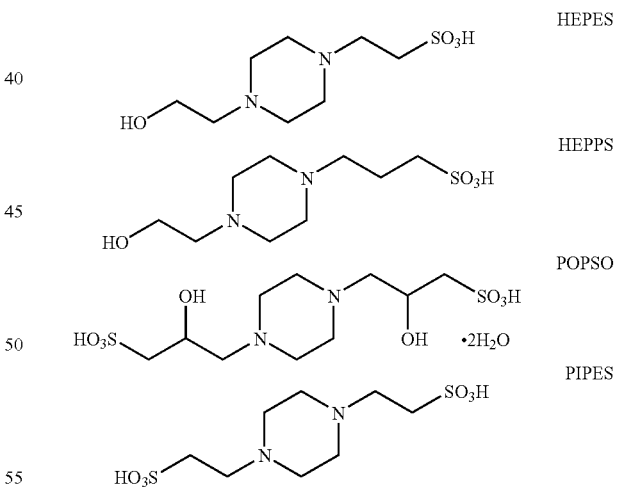

The concentration of the buffer may be appropriately selected according to the type of the buffer within the range where the pH of the antigen activation solution is kept within an appropriate range. For example, the concentration of HEPPS is preferably from 10 to 100 mM.

The antigen activation solution according to the present embodiment may contain a substance for promoting the removal of impurities in the sample for liquid based cytology. Examples of the substance include thiol compounds such as acetylcysteine and 2-mercaptoethanol.

The antigen activation solution according to the present embodiment may additionally contain a chelator. Examples of the substance include ethylenediamine tetraacetate (EDTA) and ethylene glycol bis(2-aminoethyl ether)-N,N,N',N'-tetraacetate (EGTA).

The antigen activation solution can be prepared by mixing an appropriate medium, preferably water, with the agent for breaking a hydrogen bond, and optionally a buffer, a substance for promoting the removal of impurities, and a chelator for removing inorganic substances.

Another aspect of the present invention is a method of activating a cell antigen including a step of contacting liquid-phase fixed cells to the antigen activation solution.

The liquid-phase fixed cells refers to the cells which have been subjected to treatment for inhibiting protein deterioration, wherein the cell morphology in the specimen is kept by mixing the specimen extracted from a living body with a fixation solution. The fixation is usually carried out using a commercial fixation solution containing an alcohol such as methanol, ethanol, or butanol, and may be carried out using a commercial fixation solution containing an aldehyde such as glutaraldehyde.

When cells fixed in the fixation solution are subjected to staining or other treatment, it is preferable that the fixation solution be removed. The method of removing the fixation solution is not particularly limited as long as it is a commonly used method. Examples of the method include centrifugation and filtration. It is more preferable that the fixation solution be removed as much as possible by washing the cell through repeated centrifugation or filtration.

After removal of the fixation solution, an antigen activation solution may be added to activate the cell antigen. The amount of the antigen activation solution for contacting cells may be appropriately selected according to the type of the specimen. For example, the amount of the antigen activation solution (the concentration of urea: 15 w/v %) added to $10^5$ cervical cells is preferably from 100 to 1000 μl, and more preferably from 250 to 600 μl.

The contacting temperature may be within a range which will not damage the cells, and is preferably room temperature, more specifically from 10 to 40° C.

It is preferable that the cells be mixed with and immersed in the antigen activation solution for a specified time. The immersion time is preferably from 5 to 60 minutes. Activation of antigen is sufficiently carried out when the immersion time is within the range. From the viewpoint of quickness of the test, the immersion time is more preferably within 30 minutes. The solution may be stirred several times during the immersion.

After the antigen is activated as described above, the antigen activation solution is removed, the cells are washed and appropriately immunostained, and the immunostained cells can be detected through, for example, identification of the cells by microscopy or flowcytometry, or observation of the cell morphology by image processing.

The above-described immunostaining may be carried out using an antibody (primary antibody) capable of recognizing an activated antigen, and may employ a method known to those skilled in the art. The antibody may be one which recognizes an activated antigen, and is labeled with, for example, an enzyme, fluorescent dye, or radio isotope (hereinafter referred to as a labeled antibody). In cases where a labeled antibody is not used as the primary antibody, a labeled antibody recognizing the primary antibody may be used as the secondary antibody to carry out immunostaining. Alternatively, a labeled antibody may be used as the tertiary antibody which recognizes the secondary antibody, in addition to the primary antibody and the secondary antibody which recognizes the primary antibody.

Examples of the method of detecting a cell related to cervical cancer include a method using the anti-NMP179 antibody against NMP179, which is one of nuclear matrix proteins in cervical epithelial cells, as the primary antibody. Examples of the cells related to cervical cancer include dysplastic cells such as cervical cancer cells.

It is a known technique that fixed cells are immunostained using an antibody, which binds to the antigen on the surface of the cells, without activating the antigen. However, through the antigen activation according to the present embodiment, even the antigen inside the cells is activated to allow immunostaining with an antibody against the antigen.

The cells immunostained as described above may be detected by a method known to those skilled in the art.

For example, the sample containing the immunostained cells is applied to a glass slide, the cells on the glass slide are observed by microscopy thereby detecting the immunostained cells. Detection of the immunostained cells by microscopy may be carried out by visual observation, or by analyzing a camera image of the cells on a glass slide using a image processing software or the like.

Figure 5:
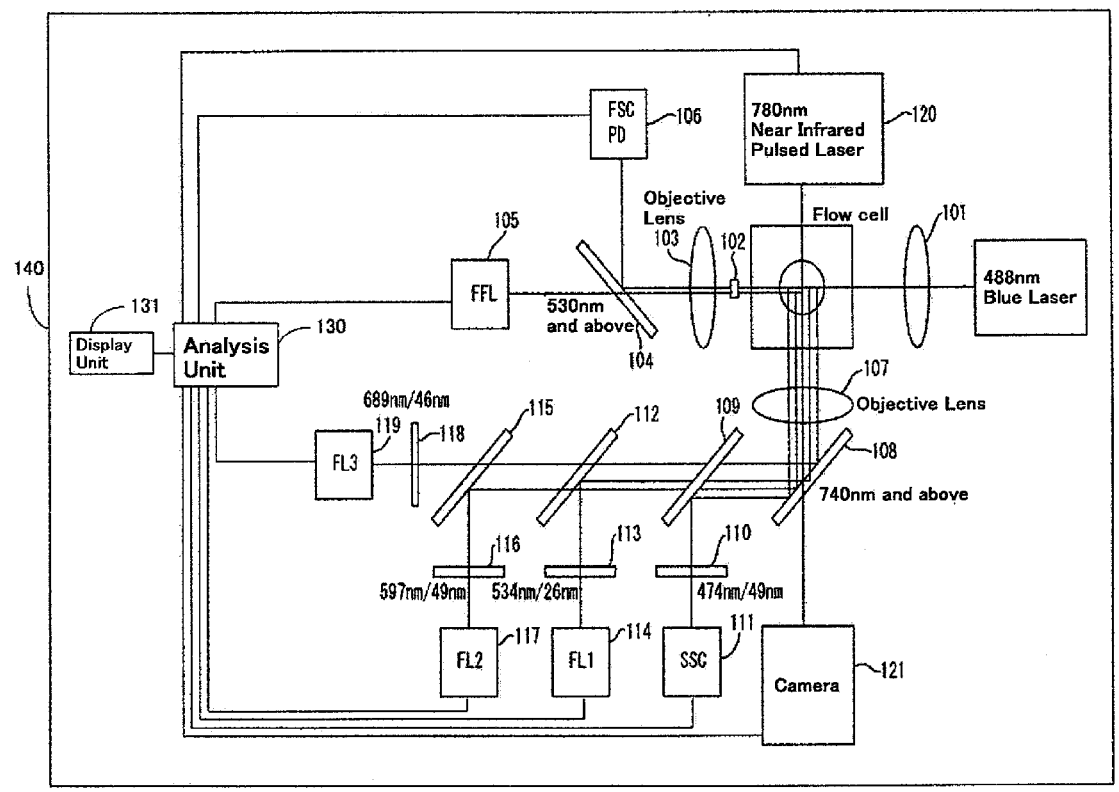
FIG. 5 shows the schematic diagram of a flowcytometer detecting immunostained cells.

Alternatively, the immunostained cells may be detected with a flowcytometer including an imaging unit having a structure as shown in FIG. 5. In the apparatus 140, F1 to F3 detect side fluorescent light which is emitted from cells and travels through a flow cell, FFL detects forward fluorescent light, FSC detects forward scattered light, SSC detects side scattered light, and a camera images the cells.

More specifically, blue laser beams (Ar ion laser beams) having an oscillation wavelength of 488 nm are passed through a lens 101 thereby being conditioned to have a flat beam profile having a minor axis of about 10 μm and a major axis of about 100 μm, and then applied to the flow cell.

Excitation light emitted through the lens 101 is passed through the flow cell and forms an image on a beam stopper 102, whereby the primary light is stopped. Fluorescent light and scattered light from the cell are collected by an objective lens 103, passed through a dichroic mirror 104 which transmits light having a wavelength of 530 nm or more, and fluorescent light with a solid angle of about 10° is introduced to a detector 105 (photomultiplier tube: PMT), where forward fluorescent light (FFL) is detected. For light having a wavelength of 530 nm or less, scattered light with a solid angle of about 100 is introduced to a detector 106 (photodiode: PD), where forward scattered light (FSC) is detected.

On the other hand, side fluorescent light and side scattered light emitted from a cell are collected by an objective lens 107 which has a high numerical aperture (NA) and is disposed at the side of the flow cell. Light outputted from the objective lens 107 is passed through a dichroic mirror 108 which reflects light having a wavelength shorter than 740 nm. The side fluorescent light and side scattered light reflected by the mirror 108 are passed through a dichroic mirror 109 which reflects light having a wavelength of 500 nm or less, and an interference filter 110 having a center wavelength of 474 nm and a transmission wavelength of 49 nm, and then introduced to a SSC detector 111 (photomultiplier tube: PMT), where side scattered light is detected. Light passed through the dichroic mirror 109 is passed through a dichroic mirror 112 which reflects light having a wavelength of 550 nm or less, and an interference filter 113 having a center wavelength of 534 nm and a transmission wavelength of 26 nm, and then introduced to a FL1 detector 114 (photomultiplier tube: PMT), where green fluorescent light is detected.

Light passed through the dichroic mirror 112 is separated into two components by a dichroic mirror 115, wherein one having a wavelength of 630 nm or less, and the other having a wavelength of 630 nm or more. One component of light is passed through an interference filter 116 having a center wavelength 597 nm and a transmission wavelength 49 nm and introduced to a FL2 detector 117 (photomultiplier tube: PMT), where orange fluorescent light is detected. The other component of light is passed through an interference filter 118 having a center wavelength of 689 nm and a transmission wavelength 46 nm and introduced to a FL3 detector 119 (photomultiplier tube: PMT), where red fluorescent light is detected.

The trapped forward scattered light (FSC), forward fluorescent light (FFL), side scattered light (SSC), green fluorescent light (FL1), orange fluorescent light (FL2), and red fluorescent light (FL3) are subjected to A/D conversion, and then inputted into an analysis unit 130. They are subjected to signal processing in the unit in real time, wherein a trigger signal is sent from the analysis unit 130 if these signals have a specific feature, and a near infrared pulse laser 120 having an oscillation wavelength of 780 nm is allowed to emit light. The pulse laser 120 serves as transmitted lighting, and light ejected from the flow cell is passed through the first dichroic mirror 108, forms an image in the camera 121, and the image data is sent to the analysis unit 130. Thus a still image of the cells having properties of specific scattered light and fluorescence is obtained.

In the analysis unit 130, the image is assessed on the basis of various kinds of optional analyses and additional images, and the result is displayed on a display unit 131.

EXPERIMENTS

The present invention is further described with reference to the following examples, but the scope of the present invention shall not be limited to these examples.

Experiment 1

Cell Fixation, Activation of Antigen, and Staining Using Cervical Cells

<Purpose>
Cervical cancer is diagnosed using cells extracted from a cervix. It is known that cervical cells remarkably change in their cell morphology depending on the stage in the menstrual cycle. More specifically, relatively strong cells with stable morphology are abundant in the early, middle, and later proliferative phases when estrogen is released. In the early, middle, and later secretory phases when progesterone is released, Doderlein's bacillus appears and dissolves the cells, so that bare nuclei appear, and impurities such as erythrocytes and mucus increase.

Accordingly, in cases where an antigen is activated after fixation of cells contained in a specimen which potentially contains other cells having different morphology, cells highly sensitive to heat may be dissolved by heat applied under a conventional antigen activation method.

The following experiments were carried out to verify that the antigen activation solution of the present invention activates an antigen with minimum change in the cells from the original state.

(1-1) Influence of the Concentration of Urea on Activation of Antigen

In order to examine the influence of the concentration of urea in the antigen activation solution on the activation of antigen, the following experiment was carried out.

<Alkaline Phosphatase (ALP)/Vector Red Staining>
A fixation solution (Preservcyt, Cytyc Corporation) was added to 50,000 cells extracted from a cervix in the secretory phase, placed in a cuvette (EZ Megafunnel, Shandon Inc), and attached to a slide (Dako corp cat#S4103) by cytospin (1500 rpm, 5 minutes: Shandon Inc.). The slide was dried overnight at room temperature.

The dried slide was mounted on a fitting for staining vat (CH-0510-075, AS ONE Corporation), transferred to a staining vat (CH-0510-065, AS ONE Corporation) filled with CytoLyt (Cytec Corporation), and allowed to stand for 30 minutes at room temperature. The slide was transferred together with the fitting for staining vat to another staining vat containing reverse osmosis water (RO water), and moved up and down five times for washing.

The slide was transferred together with the fitting for staining vat to another staining vat filled with an antigen activation solution containing 0%, 10 w/v %, 20 w/v %, or 30 w/v % of urea (and 10 mM EGTA and 50 mM HEPPS having a pH of 9.0 as additional components), and allowed to stand for 30 minutes at room temperature thereby activating the antigen.

The slide was mounted on a fitting for staining vat, and transferred to another staining vat filled with an EGTA-containing cleaning solution (containing 50 mM Tris-HCl, 0.3 M NaCl, 0.1% Tween-20, 0.1% Brij, and 10 mM EGTA), and allowed to stand for 5 minutes at room temperature.

Subsequently, the slide was washed with an EGTA-free cleaning solution (containing 50 mM Tris-HCl, 0.3 M NaCl, 0.1% Tween-20, and 0.1% Brij), mounted on a fitting for staining vat, transferred to another staining vat filled with an EGTA-free cleaning solution, and allowed to stand for about 10 minutes at room temperature (the step is hereinafter referred to as washing step). All the cleaning solutions used in the following steps are EGTA-free ones.

The slide was taken out one by one, the glass slide was wiped with Kimwipe or the like except for the areas having the cells, and the areas having the cells were surrounded with Pap Pen (Dako S2002). The slide was placed in a humidity cabinet, and a cleaning solution was dropped thereon. Dropping of a solution onto the slide in the following steps was carried out in a humidity cabinet, and the slide was allowed to stand therein.

A blocking solution (containing 4% of Normal Rabbit Serum Dako X0902, 0.5% of BSA, 25 mM Tris-HCl, 0.15M NaCl, 0.1% Tween-20, and 0.1% Brij) was dropped onto the slide, and the slide was allowed to stand for 30 minutes at room temperature. The glass slide was erected to sweep away the liquid from the slide, then 250 µl of a primary antibody solution (anti-NMP179 antibody, Matritech, 0.1 µg/mL) was dropped onto the slide, and the slide was allowed to stand for 1 hour at 25° C.

Subsequently, a secondary antibody, Rabbit anti Mouse IgG (APAAP kit Dako #Z0259) was diluted 80 times with 25 mM TBS, and 500 µl of the dilution was dropped onto the slide. The slide was allowed to stand for 15 minutes at 37° C.

Subsequently, a tertiary antibody, Alkaline phosphatase-anti-alkaline phosphatase complex solution (APAAP kit: DAKO #D0651) was diluted 40 times with 25 mM TBS, and 500 µl of the dilution was dropped onto the slide. The slide was allowed to stand for 15 minutes at 37° C.

Subsequently, a secondary antibody, Rabbit anti Mouse IgG (APAAP kit Dako #Z0259) was diluted 80 times with 25 mM TBS, and 500 µl of the dilution was dropped onto the slide. The slide was allowed to stand for 10 minutes at 37° C.

Subsequently, a tertiary antibody, Alkaline phosphatase-anti-alkaline phosphatase complex solution (APAAP kit: DAKO #D0651) was diluted 40 times with 25 mM TBS, and 500 μl of the dilution was dropped onto the slide. The slide was allowed to stand for 10 minutes at 37° C. thereby carrying out antigen-antibody reaction. Thereafter, the slide was subjected to a washing step.

The first, second, and third liquids of VECTOR SK-5100 Alkaline Phosphatase Substrate Kit 1 (vecter Labs) were sequentially added in four drops to a diluting solution (10 ml of 200 mM Tris-HCl (pH8.4)+100 μl of 100 mM Levamisole+10 μl of 100% Tween20), and 500 μl of the dilution was dropped onto the slide. The slide was allowed to stand for 30 minutes at room temperature kept away from light thereby carrying out staining. The slide was washed with 25 mM TBS, RO water, and then tap water.

A Mayer's hematoxylin stain solution (Muto Pure Chemicals Co., Ltd.) was diluted three times, filtered through a filter paper (ADVANTEC qualitative filter paper No. 1), and then placed in a staining vat. The slide was transferred to the vat together with the fitting for staining vat, allowed to stand for 1 minute at room temperature thereby carrying out counter staining. After the staining treatment, the slide was washed with tap water.

The slide was treated as follows thereby carrying out dehydration and penetration treatment.

95% EtOH immersion for 1 minute at room temperature
  95% EtOH immersion for 1 minute at room temperature
  100% EtOH immersion for 1 minute at room temperature
  100% EtOH immersion for 1 minute at room temperature
  100% xylene immersion for 1 minute at room temperature
  100% xylene immersion for 5 minutes at room temperature
  Finally, the slide was encapsulated with Clarion (Biomeda M05).

FIG. 1 shows the micrographs of the obtained samples. FIG. 1 indicates that the intensity of immunostaining increases with the increase in the concentration of urea.

Figure 2:
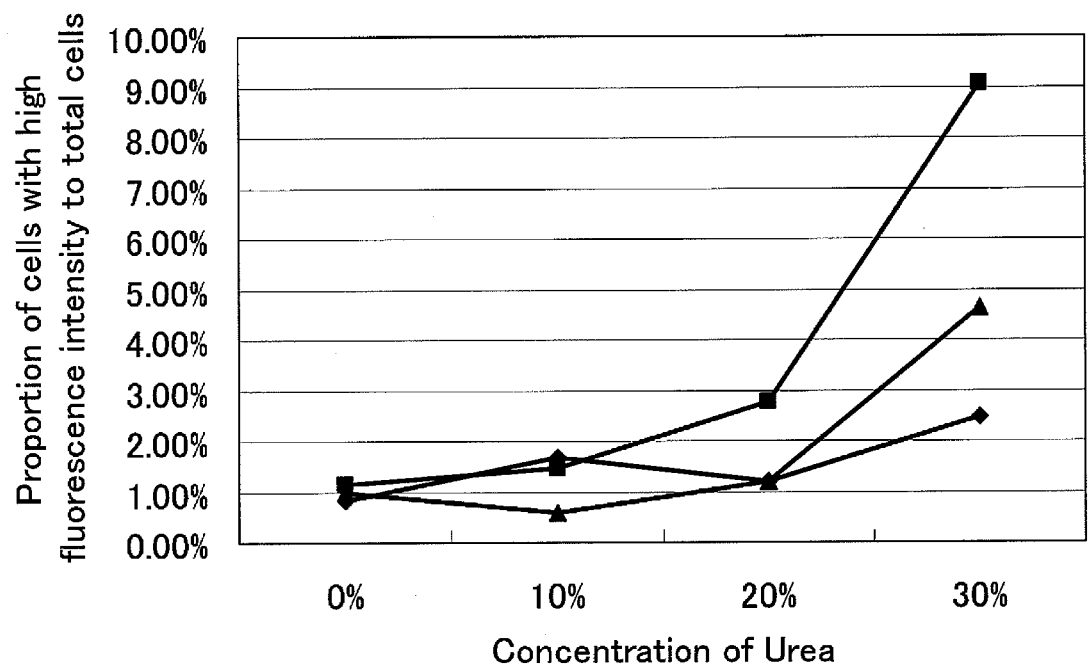
FIG. 2 shows the graph representing the relationship between the concentration of urea and the proportion of cells with a high fluorescence intensity to total cells.

In place of the ALP/vector red staining, horseradish peroxidase (HRP)/tyramide staining (the method is described below) was carried out, and the number of all cells was counted by measuring forward scattered light and side scattered light using the flowcytometer having a structure shown in FIG. 5. Subsequently, the number of cells with a high fluorescence intensity (the number of cells with a green color fluorescence intensity of 50 to 254) was counted by measuring forward scattered light and green color fluorescent light. FIG. 2 shows the graph representing the relationship between the concentration of urea and the proportion of cells with a high fluorescence intensity to total cells. FIG. 2 shows the results of measurements of different three specimens.

These results indicate that the proportion of cells with a high fluorescence intensity increases with the increase in the concentration of urea, and that the increase in the concentration of urea improves the efficiency of immunostaining, or improves the effect of activation of antigen.

<Horseradish Peroxidase (HRP)/Tyramide Staining>

$10^5$ cells were extracted from a cervix in the secretory phase, and added a fixation solution (Preservcyt, Cytyc Corporation). The solution was placed in an Eppendorf tube, and centrifuged for 1 minute at 10,000 rpm using a centrifugal machine (HITACHI CF 15R). The supernatant was removed, 750 μl of a 0.05% Tween-containing phosphate buffer normal saline solution (PBS-T, pH 7.4) was added to the precipitate, the mixture was centrifuged under the same conditions as described above, and the supernatant was removed. The obtained cells were used for fixation, and subjected to the following antigen activation.

500 μl of an antigen activation solution containing 0%, 10 w/v %, 20 w/v %, or 30 w/v % of urea (and 10 mM EGTA and 50 mM HEPES having a pH of 9.0 as additional components) was added to the cells, and lightly mixed at room temperature. The solution was allowed to stand for 15 minutes, mixed twice, and allowed to stand again for 15 minutes at room temperature. The solution was centrifuged under the same conditions as described above, and the supernatant was removed.

750 μl of PBS-T was added to the precipitate, and the mixture was centrifuged in the same manner as described above, and the supernatant was removed. The washing process was repeated three times.

1 ml of 2% hydrogen peroxide water diluted with PBS was added to the cells activated as described above, and shaken at 4 rpm for 30 minutes at room temperature. The solution was centrifuged, the supernatant was removed, and 750 μl of PBS-T was added. 750 μl of a 0.5% blocking solution (TSA blocking, Perkin Elmer) was added, and the mixture was shaken at 4 rpm for 30 minutes at room temperature. Subsequently, the solution was centrifuged, and the supernatant was removed.

400 μl of a solution of horseradish peroxidase (HRP)-labeled anti-NMP179 antibody recognizing a nuclear matrix protein (Matritech, 2 μg/ml) was added to the precipitate, and the mixture was shaken at 4 rpm for 30 minutes at room temperature. The solution was centrifuged, the supernatant was removed, and the cells were washed with 750 μl of PBS-T three times. 200 μl of a tyramide staining solution (Fluorescein Tyramide Reagent, Perkin Elmer) was added to the cells, and the solution was shaken at 4 rpm for 30 minutes at room temperature kept away from light. Subsequently, the cells were centrifuged, the supernatant was removed, and the precipitate was washed with 750 μl of PBS-T three times.

The obtained cells were subjected to the measurement by flowcytometry.

Experiment 2

Influence of Treatment with Antigen Activation Solution

In order to examine the influence of the antigen activation solution on diagnosis, the following experiment was carried out.

Conventionally, cervical cancer has been diagnosed based on Papanicolaou stain. In the diagnosis based on Papanicolaou stain, cells extracted from a cervix are stained with a Papanicolaou stain solution, and the morphology and stained conditions of the stained cells and nuclei are observed by microscopy, and the cellular atypism is determined. The method is a classification method based on that the Papanicolaou stain solution stains the nucleus of a benign cell and the nucleus of a malignant dysplastic cell in different colors. According to the classification by Japan Association of Obstetricians & Gynecologists, evaluations are made according to the classification shown in Table 1.

TABLE 1

| Class | | Status |
|---|---|---|
| I | | Normal |
| II | | Abnormal cell but benign |
| III | IIIa | Mild dysplasia is supposed |
| | IIIb | Severe dysplasia is supposed |
| IV | | Carcinoma in situ is supposed |
| V | | Invasive cancer (including invasive microcancer) is supposed |

Then, the cells before and after the treatment with the antigen activation solution were subjected to Papanicolaou stain, and examined whether the antigen activation treatment with the antigen activation solution gives influences on the results of Papanicolaou's evaluation.

The specimens were cells extracted from patients in the early proliferative phase (1 specimen), middle proliferative phase (1 specimen), later proliferative phase (1 specimen), early secretory phase (2 specimens), middle secretory phase (1 specimen), later secretory phase (3 specimens), and postmenopausal phase (4 specimens).

These specimens extracted were fixed with Preservcyt (Cytyc Corporation) after the extraction.

Some of the fixed specimens was subjected to Papanicolaou stain, observed by microscopy, and assessed based on Papanicolaou's evaluation. Papanicolaou stain was carried out using a Papanicolaou stain solution manufactured by Muto Pure Chemicals Co., Ltd.

500 µl of an antigen activation solution containing 15 w/v % of urea (containing 10 mM EGTA and 50 mM HEPES having a pH of 9.0 as additional components) was added to the remaining specimens, and lightly mixed at room temperature. The solution was allowed to stand for 15 minutes, mixed twice, and allowed to stand again for 15 minutes at room temperature. The solution was centrifuged under the same conditions as described above, and the supernatant was removed. 750 µl of PBS-T was added to the precipitate, and the mixture was centrifuged in the same manner as described above, and the supernatant was removed. The washing process was repeated three times.

The cells subjected to the antigen activation were subjected to Papanicolaou stain in the same manner as described above. The results are shown in Table 2.

TABLE 2

| | | | Evaluation of Papanicolaou test | |
| --- | --- | --- | --- | --- |
| Specimen No. | Menstrual cycle | | Before antigen activation | After antigen activation |
| 1 | Proliferative phase | Early | II | II |
| 2 | | Middle | II | II |
| 3 | | Later | IV | IV |
| 4 | Secretory phase | Early | II | II |
| 5 | | Early | IIIb | III |
| 6 | | Middle | IIIa | III |
| 7 | | Later | IIIa | III |
| 8 | | Later | II | II |
| 9 | | Later | II | II |
| 10 | Postmenopausal phase | | IIIa | III |
| 11 | | | II | II |
| 12 | | | II | II |
| 13 | | | II | II |

As indicated by Table 2, the results of evaluation of the Papanicolaou test (Papanicolaou's evaluation) based on the conventional method (the results of the evaluation before the antigen activation treatment with the antigen activation solution of the present example) are in good agreement with the results of the Papanicolaou's evaluation after the antigen activation treatment with the antigen activation solution of the present example (agreement=100%). This fact indicates that the treatment with the antigen activation solution does not affect the morphology of cells or nuclei.

Experiment 3

Cell Detection by Image Processing

Figure 3:
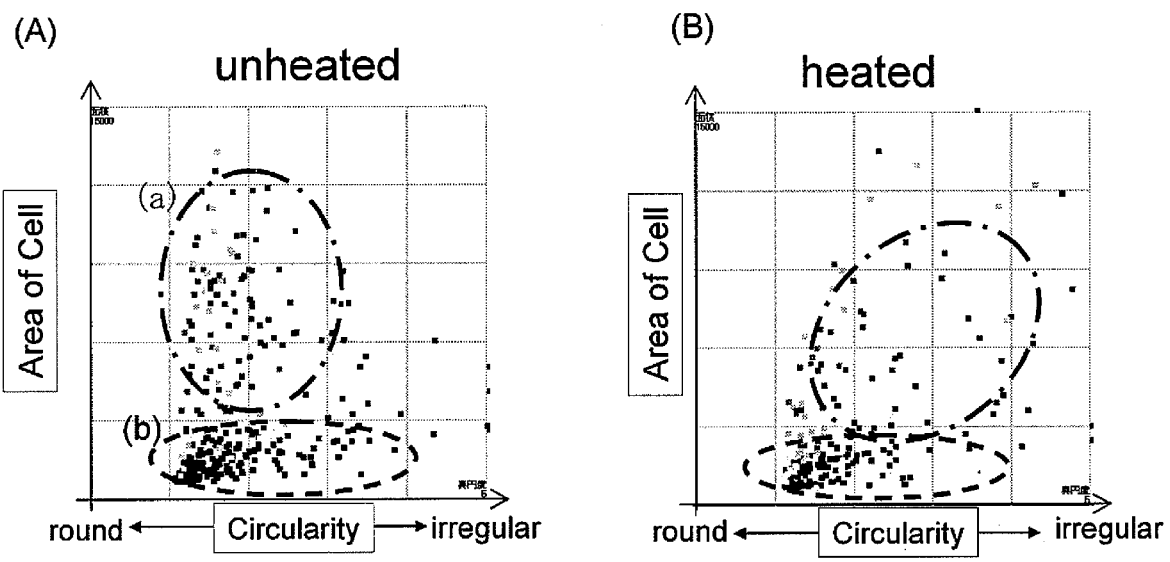
FIG. 3 (A) shows the scattergram of unheated cells, and FIG. 3 (B) shows a scattergram of heated cells.

Diagnosis of cervical cancer requires squamous cells. The cells keep their shapes to a degree in the proliferative phase with no breakage by swelling or other causes, so that their images appear in the region expressed by the chained line (a) in FIG. 3A (squamous cell-appearing region). On the other hand, images of impurities such as bare nuclei and broken cells appear in the region expressed by the dashed line (b) in FIG. 3A (impurity-appearing region). For example, when the specimen used in FIG. 3A is heated at 100° C. under the conventional antigen activation method, as shown in FIG. 3B, bare nuclei and cell fragments increase, and less cells keep their shapes. In addition, the specimen in the secretory phase contains much cells dissolved by the influence of Doderlein's bacillus, so that lots of bare nuclei and dissolved cells appear in the lower region of a graph as expressed by the region (b) in FIG. 3B (impurity-appearing region). The horizontal axis of FIG. 3 represents cell circularity (a cell approaches a circle or round as the value of circularity approaches to the left end, and increases in asperities or irregularity as the value approached to the right end), and the vertical axis represents the cell area.

The same specimens in the early, middle, and later proliferative phases, and early, middle, and later secretory phases as those used in Example 2 were individually subjected to the antigen activation treatment with an antigen activation solution containing 15 w/v % of urea in the same manner as Example 2. After the treatment, the specimen was subjected to tyramide staining, and the specimen containing the stained cells was dropped onto a glass slide. The glass slide was mounted on an inverted microscope, AxioVert 200 manufactured by Zeiss (condenser: LD condenser (N.A.0.55) Ph2, objective lens: 20 times, LD AchroPlan (N.A.0.4) Ph2, fluorescent filter: filter set #17), and the cells on the glass slide were imaged with an exposure time of 1 second using a CCD camera, AxioCamHRc manufactured by Zeiss. The image was analyzed by Image-Pro Plus (ver. 4.5.1.23) manufactured by Media Cybernetics, and the area and circularity of the imaged cells were calculated. On the basis of the calculation result, a scattergram composed of two axes of cell area (vertical axis) and circularity (horizontal axis) was prepared.

Figures 1, 4:
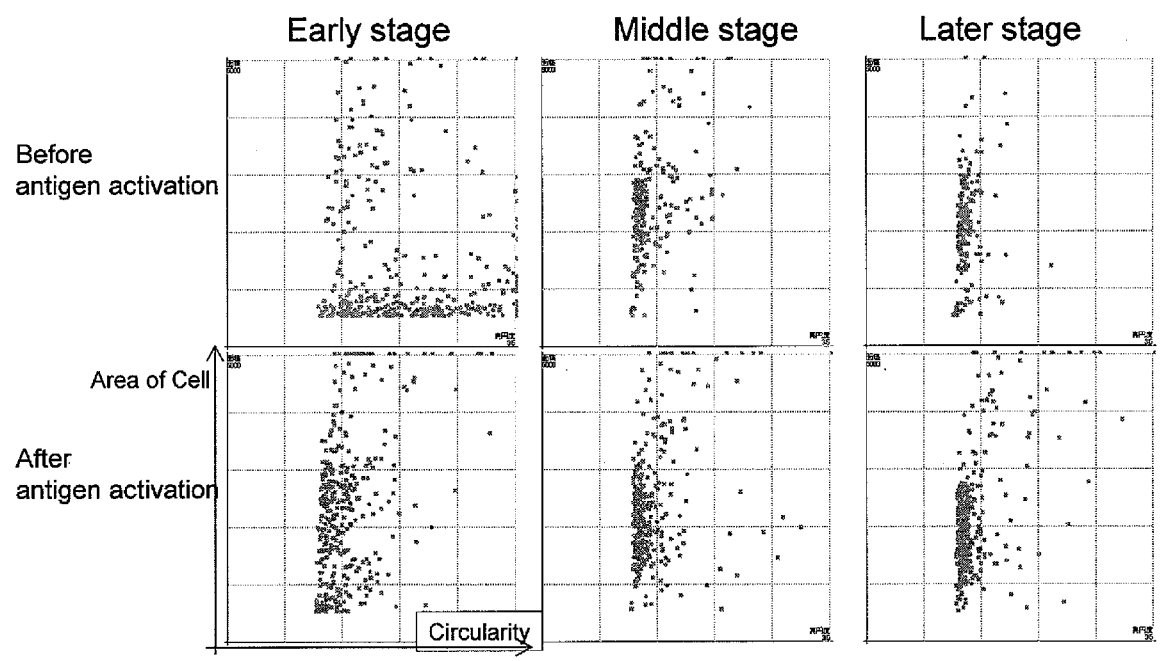
Figures 2, 4:
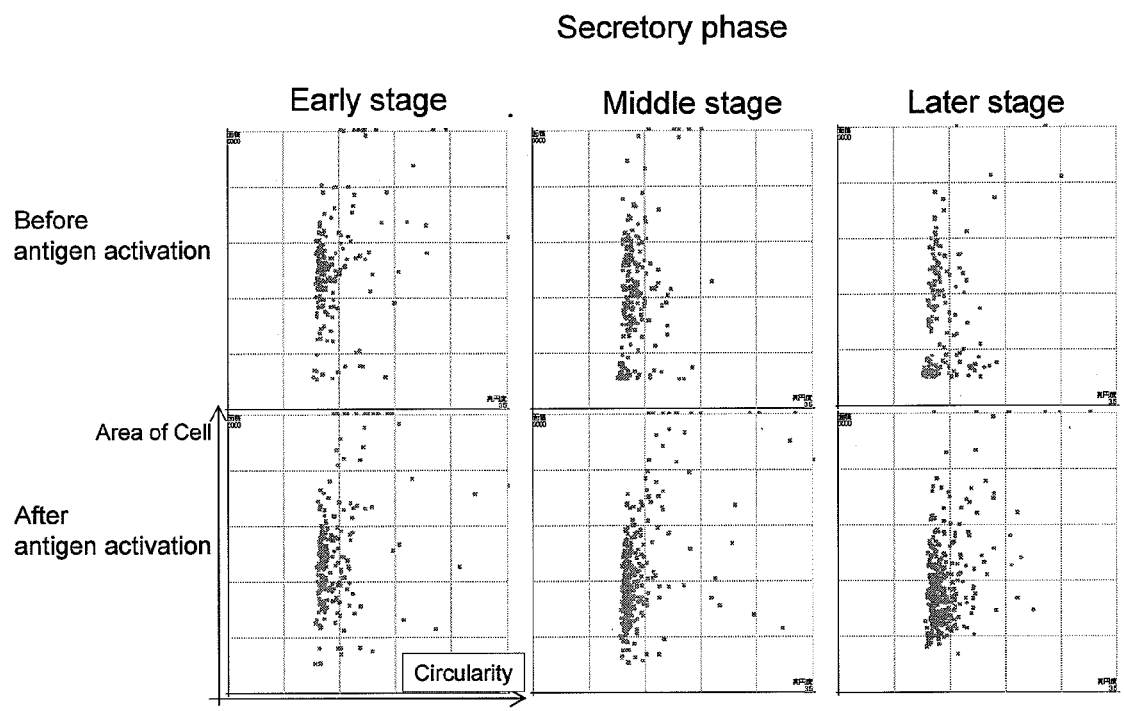

The scattergram is shown in FIG. 4. As is evident from FIG. 4, for all the specimens in any stages of the menstrual cycle, the number of cells appearing in the squamous cell appearing region scarcely changed regardless the antigen activation treatment with the antigen activation solution. This fact indicate that squamous cells essential for the diagnosis of cervical cancer little change in their morphology.

Figure 6:
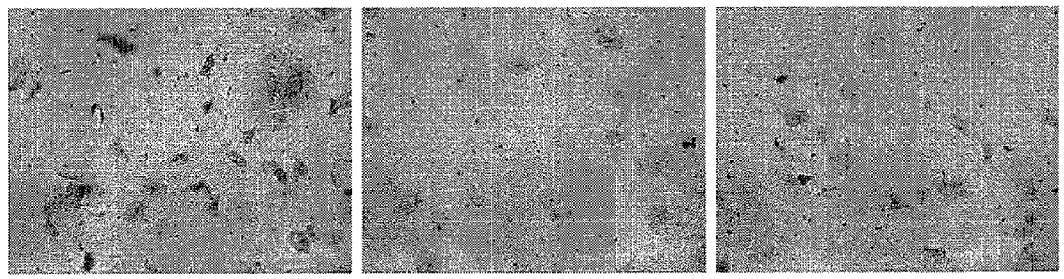
FIG. 6 shows micrographs of the specimens extracted from subjects in the later secretory phase of the menstrual cycle.
Figure 6:
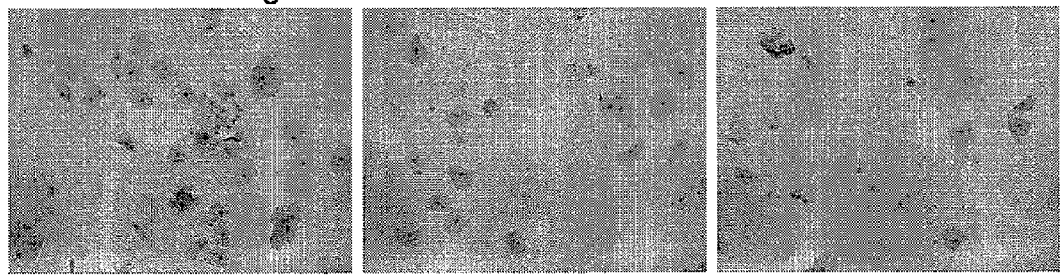

It is also indicated that the treatment with the antigen activation solution removed impurities such as bare nuclei, broken cells, and erythrocytes appearing in the impurity-appearing region. FIG. 6 shows micrographs representing the fact. The micrographs in FIG. 6 show the specimens extracted from subjects in the later secretory phase of the menstrual cycle. The upper micrographs are images of specimens subjected to Papanicolaou stain without the antigen activation treatment, and the lower micrographs are image of specimens subjected to Papanicolaou stain after the antigen activation treatment. In the upper micrographs showing the specimens without the antigen activation treatment, erythrocytes and other impurities are abundantly observed as well as the squamous cells to be detected. In the lower micrographs showing the specimens with the antigen activation treatment, squamous cells to be detected keep their morphology, while erythrocytes and other impurities are scarcely observed. These facts indicate that the treatment with the antigen activation solution removes impurities. The reduction of impurities by the treatment with the antigen activation solution relieves the burden to the speculum used for microscopic cytodiagnosis, because the specimen contains less substances other than the cells to be detected. In addition, when cells are detected based on scattered light information or fluorescent light information measured using a flowcytometer, the measurement accuracy is improved due to less impurities. Furthermore, when cells are detected based on a cell image, inclusion of fewer impurities facilitates image recognition by an image recognition software thereby facilitating automatization of image analysis of cells.

What is claimed is:

1. A method for activating an antigen of a cell fixed by a nonbridging fixation solution, comprising:
   providing an antigen activation solution comprising urea and a chelator;
   providing a cell fixed by a nonbridging fixation solution; and
   activating an antigen of the cell substantially without affecting cell morphology under a temperature of 10 to 40 degrees Celsius by contacting the cell fixed by the nonbridging fixation solution with the antigen activation solution under a temperature of 10 to 40 degrees Celsius.

2. The method according to claim 1, wherein a concentration of the urea in the antigen activation solution is 10 to 30 w/v %.

3. The method according to claim 1, wherein a concentration of the urea in the antigen activation solution is 10 to 15 w/v %.

4. The method according to claim 1, wherein pH of the antigen activation solution is 7 to 9.

5. The method according to claim 1, wherein the antigen activation solution comprises a buffer represented by formula (I):

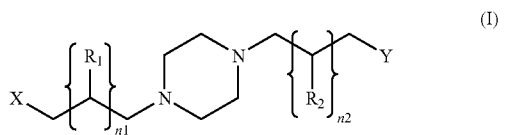

wherein X represents —OH or —SO$_3$, Y represents —OH or SO$_3$, R1 represents a hydrogen atom or —OH, R2 represents a hydrogen atom or —OH, n1 is 0 or 1, and n2 is 0 or 1.

6. The method according to claim 5, wherein the buffer comprises at least one selected from the group consisting of 2-[4-(2-hydroxyethyl)-1-piperazinyl]ethanesulfonic acid, 3-[4-(2-hydroxyethyl)-1-piperazinyl]propanesulfonic acid, piperazine-1,4-bis(2-hydroxy-3-propanesulfonic acid) dihydrate, and piperazine-1,4-bis(2-ethanesulfonic acid).

7. The method according to claim 1, wherein the chelator comprises at least one selected from the group consisting of ethylenediamine tetraacetate and ethylene glycol bis(2-aminoethyl ether)-N,N,N',N'-tetraacetate.

8. A method for detecting a cell fixed by a nonbridging fixation solution, comprising:
   providing an antigen activation solution comprising urea and a chelator;
   providing a cell fixed by a nonbridging fixation solution;
   activating an antigen of the cell substantially without affecting cell morphology under a temperature of 10 to 40 degrees Celsius by contacting the cell fixed by the nonbridging fixation solution with the antigen activation solution under a temperature of 10 to 40 degrees Celsius;
   immunostaining the cell whose antigen is recognized by an antibody which can bind to the activated antigen; and
   detecting the stained cell.

9. The method according to claim 8, wherein the concentration of the urea in the antigen activation solution is 10 to 30 w/v %.

10. The method according to claim 9, wherein the concentration of the urea in the antigen activation solution is 10 to 15 w/v %.

11. The method according to claim 8, wherein the stained cell is detected by a flowcytometry.

12. The method according to claim 8, wherein the contacting is conducted at the temperature of 10 to 40 degrees Celsius.

13. The method according to claim 8, wherein the cell is a dysplastic cell derived from uterine cervix of a living body.

14. The method according to claim 8, wherein the antigen is a protein expressed specifically in a cervical cancer cell.

15. The method according to claim 1, wherein the activating step comprises contacting the cell fixed by the nonbridging fixation solution and the antigen activation solution for 5 to 60 minutes.

16. The method according to claim 1, wherein the activating step comprises contacting the cell fixed by the nonbridging fixation solution and the antigen activation solution for 5 to 30 minutes.

17. The method according to claim 8, wherein the activating step comprises contacting the cell fixed by the nonbridging fixation solution and the antigen activation solution for 5 to 60 minutes.

18. The method according to claim 8, wherein the activating step comprises contacting the cell fixed by the nonbridging fixation solution and the antigen activation solution for 5 to 30 minutes.

* * * * *